United States Patent [19]

Larsen

[11] Patent Number: 4,656,224

[45] Date of Patent: Apr. 7, 1987

[54] RADIOPAQUE THERMOSET POLYMER

[75] Inventor: Eric R. Larsen, Midland, Mich.

[73] Assignee: The Dow Chemical Company, Midland, Mich.

[21] Appl. No.: 878,508

[22] Filed: Jun. 23, 1986

Related U.S. Application Data

[63] Continuation-in-part of Ser. No. 728,411, Apr. 29, 1985, abandoned.

[51] Int. Cl.$^4$ .............................................. C08L 67/06
[52] U.S. Cl. ...................................... 525/40; 525/36; 424/5
[58] Field of Search .................. 525/34, 36, 40; 424/5

[56] References Cited

U.S. PATENT DOCUMENTS

| | | | |
|---|---|---|---|
| 3,715,331 | 2/1973 | Molnar | 523/117 |
| 4,134,811 | 1/1979 | De Poortere | 204/159.15 |
| 4,406,878 | 9/1983 | De Boer | 424/5 |

OTHER PUBLICATIONS

Bjorksten, Polyesters and their Applications Reinhold Publishing Corp. pp. 13–14 (1956).

*Primary Examiner*—Lewis T. Jacobs
*Assistant Examiner*—Patricia A. Short

[57] ABSTRACT

Compositions consisting essentially of thermoset polymers prepared by copolymerizing a solution of an iodine containing, crosslinkable, unsaturated polyester resin dissolved in a vinyl monomer are disclosed. These compositions have been found to be useful as radiopaque agents and in the manufacture of radiopaque, flame retardant articles.

12 Claims, No Drawings

RADIOPAQUE THERMOSET POLYMER

CROSS-REFERENCE TO RELATED APPLICATION

This is a continuation in part of application Ser. No. 728,411 Filed Apr. 29, 1985, now abandoned.

BACKGROUND OF THE INVENTION

This invention relates to solid, infusible, iodine-containing polymers usable as X-ray contrast agents for obtaining X-ray photographs of the alimentary tract, and as solid reinforced plastics for the manufacture of radiopaque, flame retardant articles.

Medical X-ray photographs of the alimentary tract are usually obtained by using barium sulfate as the contrast agent. See U.S. Pat. No. 3,017,329. Barium sulfate is a very dense, slightly soluble, inorganic salt which tends to agglomerate and settle out in the stomach. While various suspending agents are used to minimize this problem, none are entirely satisfactory. Barium sulfate has also been reported to cause constipation if not promptly removed from the system, and occassionally, enough is absorbed to produce toxic reactions. U.S. Pat. Nos. 3,891,605; 3,700,957; and 3,507,933 disclose the use of brominated compounds as flame retardant, reinforced plastics, but not as radiopaque agents.

Iodine containing compounds have also been employed as X-ray contrast agents. These compounds, however, are usually absorbed into the body, and then metabolized. The water-soluble iodine containing compounds are usually sufficiently osmotically active at the doses required for visualization, but movement through the tract is rapid and often leads to catharsis.

The iodine containing X-ray contrast agents known in the art have generally employed iodobenzoates with a vinyl resin (U.S. Pat. No. 3,645,955); polyurethane resins (U.S. Pat. Nos. 4,282,876 and 4,250,072); and an alkoxyalkyl ester which is not claimed as a polyester (U.S. Pat. No. 3,361,700). U.S. Pat. No. 3,852,341 discloses the use of triiodobenzoic acid polymers as edible radiopaque agents. However, none of these polymers have been claimed as radiopaque, flame retardants. Japanese Pat. No. 71222579-R discloses the use of trimethyliodide polyethylene/propylene polymers as flame retardant reinforced plastics, but not as radiopaque agents.

It is thus an object of this invention to provide a crosslinked unsaturated iodinated polyester resin that, when ground, produces an excellent X-ray contrast agent. It is a further object of this invention to provide an X-ray contrast agent that does not tend to settle out in the stomach or intestines, but clings to the fine ridges and grooves in the stomach and intestinal lining to give good detailed pictures. It is also an object of this invention to provide a polymer that is water-insoluble and osmotically inactive, and not absorbed into the body. It is a further object of this invention to provide a polymer usable as a solid reinforced plastic for the manufacture of radiopaque, flame retardant, articles.

DETAILED DESCRIPTION OF THE INVENTION

This invention relates to a composition consisting essentially of a thermoset polymer prepared by copolymerizing a solution of iodine containing crosslinked unsaturated polyester resin dissolved in a vinyl monomer. This invention further relates to the use of the claimed composition as a radiopaque agent and as a solid reinforced plastic for the manufacture of radiopaque, flame retardant, articles.

So far as is known at this time, any iodine containing crosslinked unsaturated polyester resin can be employed for the purposes of this invention. Unsaturated and saturated anhydrides, acids, acid chlorides, and vinyl monomers, normally employed in the manufacture of unsaturated polyester resins, can be employed for the purposes of this invention. Likewise, any iodohydric alcohol, including diiodohydrin, triiodohydrin, and mixtures thereof, may be employed for the purpose of this invention. The iodo compound may contain minor amounts of the bromo- or bromo-iodo- analogs.

It is preferred that the unsaturated polyester resin is prepared by reacting pentaerythritol diiodohydrin with a mixture of at least one aliphatic unsaturated dicarboxylic acid, its anhydride, or its acid chloride having from 4 to 5 carbon atoms in the molecule and an aromatic dicarboxylic acid selected from the group consisting of phthalic acid and hydrogenated phthalic acid, their anhydride, or their acid chloride, in which mixture the molar ratio of aliphatic acid to aromatic acid is from 3:1 to 1:2. Examples of the alphatic unsaturated dicarboxylic acid or its anhydride include maleic, fumaric, citraconic and acetylenedicarboxylic.

It is preferred, however, that the polyester resin employed be prepared by reacting pentaerythritol diiodohydrin with maleic anhydride and phthalic anhydride. It is further preferred that the resin solid contain about 50 to 60 percent iodine and have an acid number of less than 60. It is also preferred that the solid particles of the cured polymer have a particle size of less than 200 mesh.

So far as is known at this time, any vinyl monomer is suitable to dissolve the polyester resin. Examples of suitable vinyl monomers include styrene, alkyl substituted styrenes such as vinyltoluene, vinylxylene, ethylvinylbenzene, isopropylstyrene, and tertbutylstyrene; and halogen substituted styrenes such as fluorostyrene, chlorostyrene, dichlorostyrene, and bromostyrene. Specific examples include orthomethylstyrene, orthochlorostyrene, metaethylstyrene, parabutylstyrene, 2,4-dichlorostyrene, 2,5-dichlorostyrene, iodostyrene, and alphamethylstyrene. It is preferred, however, that the vinyl monomer be styrene. The resin solid will be dissolved in the monomer and the resulting solution will contain from 1 to 40 percent iodine.

The composition of this invention may be employed as a solution in the vinyl monomer or as a solid polymer made by curing the solution.

The novel compounds disclosed in this invention are very useful as X-ray contrast agents. After the application of the contrast agent of the present invention, the test object is exposed to X-rays whereupon photographs may be taken or the image observed directly on a fluorescent screen. The dose of the contrast agent administered depends upon the category of the investigation.

Because the compositions are radiopaque, i.e., opaque to X-rays, surgical products prepared from them can be readily visualized by fluoroscopic devices or in X-ray photographs. This facilitates insertion, observation during use, and the location of broken fragments. The composition may, for example, be employed to manufacture surgical tubing for stomach, nasal, ureteral, vein intubation, heart, thoracic catheters, and the like. Radiopaque compositions are also employed to make sheeting for location and protection purposes, surgeon's gloves and prosthetic appliances and toy parts. However, due to the solid polymer's inflexibility, to employ it to a device needing flexibility, such as gloves, the ground up polymer must be imbedded into latex or another polymer, i.e., polyvinylchloride, polyethylene, etc.

The X-ray contrast agents may also be used to photograph one of the body cavities. The contrast agents may be in the form of a mixture, such as an aqueous suspension, or a solid with a physiologically acceptable solid carrier. One example of the different body cavities which can be visibilized by the compounds of the invention is the gastro-intestinal tract. The contrast producing agent is administered orally in solid or solution form, whereupon it passes the gastro-intestinal duct without being appreciably absorbed. It is also possible to visibilize intestines by administering the contrast agent through the rectum in the form of an enema.

The X-ray contrast agents of the present invention may also be employed to make toys radiopaque to aid visualization if swallowed.

Because the contrast agents of the present invention contain hydroxyl groups, they possess good physiological and solubility properties. The toxicity is thus low which will eliminate the possibility of toxic reactions within the body.

Now in order that those skilled in the art may better understand how the present invention can be practiced, the following example is given by way of illustration and not by way of limitation. The pentaerythritol diiodohyrdin employed in the preparation of the polyester resin contained approximately 75 percent pentaerythritol diiodohydrin, 23 percent bromoiodohydrin and 1 percent dibromohydrin on a solvent free basis by GLG-area percent basis.

The iodinated unsaturated polyester resin was prepared by equipping a two liter glass resin kettle with a mechanical stirrer, a temperature controlled heat source, a Dean-Stark tube reflux condenser, and a nitrogen sparge charged with 2.8 moles of maleic anhydride and 1.2 moles of phthalic anhydride. The anhydrides were then heated to 100° C. to melt them.

Over a 15 minute period, 4.5 moles of pentaerythritol diiodohydrin and 0.023 moles of p-toluenesulfonic acid was added to the molten anhydrides. The temperature of the mixture was then raised to 145° C. over a period of an hour. The mixture was reacted for an additional 1.5 hours at 145° C. during which time 187 ml of water was collected in the Dean-Stark tube. The acid number of the molten product was less than 59.

The reaction mixture was then cooled at approximately 60° C. During cooling, 750 ml of methylene chloride was added. After the mixture was cooled to room temperature, it was washed with a solution of 49 g of sodium metabisulfite in 500 ml of water, separated, and washed with five 500 ml portions of water. The organic layer was then stripped on a Buchi rotary-evaporator to remove $CH_2Cl_2$ to give a thick viscous resin.

A 200 g aliquot of the above prepared resin was dissolved in about 85 g of styrene. One percent or 2.8 g of benzoyl peroxide was dissolved into the resin. The resin was then cured between glass plates in a 110° C. oven for one hour. The resulting cured resin was a clear, water white, solid polymer with a Barcol hardness of 20 to 30 and containing 34 percent by weight of iodine and 4.1 percent by weight bromine. The polymer had a density of 1.63 g/cc. The polymer was then tested for flammability according to ASTM D-2863-70, "Flammability of Plastics Using the Oxygen Index Method," and had an OI of 32.0.

The polymer was then broken up and ground to a powder. The materal was then passed through a 325 mesh screen (45 microns).

A suspension of the iodinated polymer was then prepared from 4 g of the ground polymer, 5.7 g of water, and 0.3 g of methylcellulose. Three milliliters of this suspension was fed to a rat weighing about 200 g, by gavage. The rat was then anesthetized with Nembutol. X-rays were taken at 0.5, 1.5, and 3.5 hours after dosing using a GE single phase X-ray machine at settings of 60 KV, 100 ma. and $\frac{1}{8}$ second. The resulting X-ray plates showed a clear outline of the stomach, intestines, etc, and were judged to be of excellent quality. There was no apparent tendency of the agent to settle out or agglomerate. The agent continued to show good detail of the stomach even after the bulk of the material had advanced well into the intestines.

What is claimed is:

1. A composition consisting essentially of a thermoset polymer prepared by copolymerizing a solution of an iodine containing crosslinkable unsaturated polyester resin dissolved in a vinyl monomer; wherein said unsaturated polyester resin is prepared by reacting pentaerythritol diiodohydrin and a mixture of at least one aliphatic unsaturated dicarboxylic acid, its anhydride, or its acid chloride having from 4 to 5 carbon atoms in the molecule and an aromatic dicarboxylic acid selected from the group consisting of phthalic acid and hydrogenated phthalic acid, their anhydrides, or their acid chlorides, in which mixture the molar ratio of aliphatic acid to aromatic acid is from 3:1 to 1:2.

2. The composition as defined in claim 1 wherein the unsaturated polyester resin is prepared by reacting pentaerythritol diiodohydrin with maleic anhydride and phthalic anhydride; and the vinyl monomer is styrene.

3. The composition as defined in claim 2 wherein the polyester resin solid contains about 50 to 60 percent bound iodine and has an acid number of less than 60.

4. The composition as defined in claim 3 wherein the solid particles of the cured polymer have a particle size of less than 200 mesh.

5. A radiopaque agent consisting essentially of a thermoset polymer prepared by copolymerizing a solution of an iodine containing crosslinkable unsaturated polyester resin dissolved in a vinyl monomer; wherein said unsaturated polyester resin is prepared by reacting pentaerytritol diiodohydrin and a mixture of at least one aliphatic unsaturated dicarboxylic acid, its anhydride, or its acid chloride having from 4 to 5 carbon atoms in the molecule and an aromatic dicarboxylic acid selected from the group consisting of phthalic acid and hydrogenated phthalic acid, their anhydrides, or their acid chlorides, in which mixture the molar ratio of aliphatic acid to aromatic acid is from 3:1 to 1:2.

6. An agent as defined in claim 5 wherein the unsaturated polyester resin is prepared by reacting pentaerythritol diiodohydrin with maleic anhydride and phthalic anhydride; and the vinyl monomer is styrene.

7. An agent as defined in claim 6 wherein the resin solid contains about 50 to 60 percent bound iodine and has an acid number of less than 60.

8. An agent as defined in claim 7 wherein the solid particles of the cured polymer have a particle size of less than 200 mesh.

9. Radiopaque, flame retardant articles consisting essentially of thermoset polymers prepared by copolymerizing a solution of an iodine containing crosslinkable unsaturated polyester resin dissolved in a vinyl monomer; wherein said unsaturated polyester resin is prepared by reacting pentaerytritol diiodohydrin and a mixture of at least one aliphatic unsaturated dicarboxylic acid, its anhydride, or its acid chloride having from 4 to 5 carbon atoms in the molecule and an aromatic dicarboxylic acid selected from the group consisting of phthalic acid and hydrogenated phthalic acid, their anhydrides, or their acid chlorides, in which mixture of the molar ratio of aliphatic acid to aromatic acid is from 3:1 to 1:2.

10. The articles as defined in claim 9 wherein the resin is prepared by reacting pentaerythritol diiodohydrin with maleic anhydride and phthalic anhydride; and the vinyl monomer is styrene.

11. The articles as defined in claim 10 wherein the resin solid contains about 50 to 60 percent bound iodine and has an acid number of less than 60.

12. The articles as defined in claim 11 wherein the solid particles of the cured polymer have a particle size of less than 200 mesh.

* * * * *